(12) United States Patent
Anderson, Jr. et al.

(10) Patent No.: US 9,961,940 B2
(45) Date of Patent: May 8, 2018

(54) VAPORIZING ASSEMBLY AND VAPOR GENERATING DEVICE

(71) Applicant: Funai Electric Co., Ltd., Osaka (JP)

(72) Inventors: James D. Anderson, Jr., Lexington, KY (US); Jason Vanderpool, Lexington, KY (US)

(73) Assignee: FUNAI ELECTRIC CO., LTD. (JP)

( * ) Notice: Subject to any disclaimer, the term of this patent is extended or adjusted under 35 U.S.C. 154(b) by 0 days. days.

(21) Appl. No.: 15/297,615

(22) Filed: Oct. 19, 2016

(65) Prior Publication Data
US 2017/0208864 A1 Jul. 27, 2017

Related U.S. Application Data

(60) Provisional application No. 62/281,804, filed on Jan. 22, 2016.

(51) Int. Cl.
*A24F 47/00* (2006.01)
*H05B 1/02* (2006.01)

(52) U.S. Cl.
CPC ......... *A24F 47/008* (2013.01); *H05B 1/0244* (2013.01); *H05B 2203/021* (2013.01)

(58) Field of Classification Search
CPC ............................. A24F 47/008; A24F 47/00
USPC .................................. 131/173–320, 328–329
See application file for complete search history.

(56) References Cited

U.S. PATENT DOCUMENTS

| | | | |
|---|---|---|---|
| 9,055,617 B2 | 6/2015 | Thorens et al. | |
| 9,351,522 B2 | 5/2016 | Safari | |
| 2013/0087160 A1 | 4/2013 | Gherghe | |
| 2015/0114409 A1 | 4/2015 | Brammer et al. | |
| 2015/0128966 A1 | 5/2015 | Lord | |
| 2015/0136158 A1 | 5/2015 | Stevens et al. | |
| 2016/0100633 A1* | 4/2016 | Gao | A24F 47/008 131/329 |
| 2016/0106153 A1* | 4/2016 | Zhu | A24F 47/008 131/329 |
| 2017/0105449 A1* | 4/2017 | Hearn | A24F 47/008 |

* cited by examiner

*Primary Examiner* — Phuong Dinh
(74) *Attorney, Agent, or Firm* — Luedeka Neely Group, PC

(57) ABSTRACT

A heater assembly for a vaporizing device, a vaporizing device containing the heater assembly, and a method for vaporizing fluid ejected by an ejection head. The heater assembly for the vaporizing device includes a vapor inlet end and a vapor outlet end, positive and negative electrodes for contact with positive and negative heater terminals on a vaporizing heater, an insulator disposed between the positive and negative electrodes, and a wick disposed between the insulator and the vaporizing heater for dispersion of liquid to be vaporized by the vaporizing heater and for back pressure control of the vaporizing device.

15 Claims, 8 Drawing Sheets

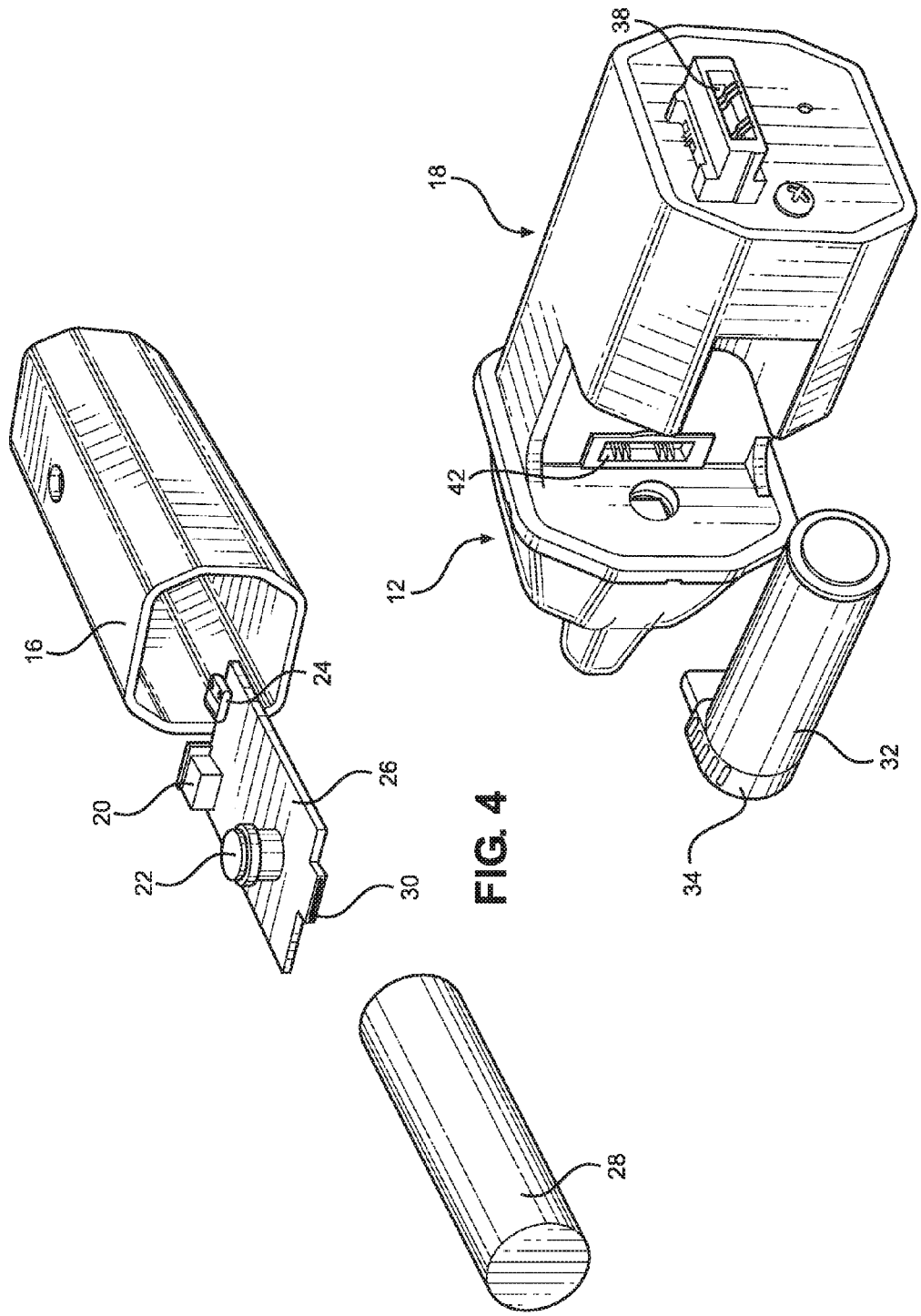

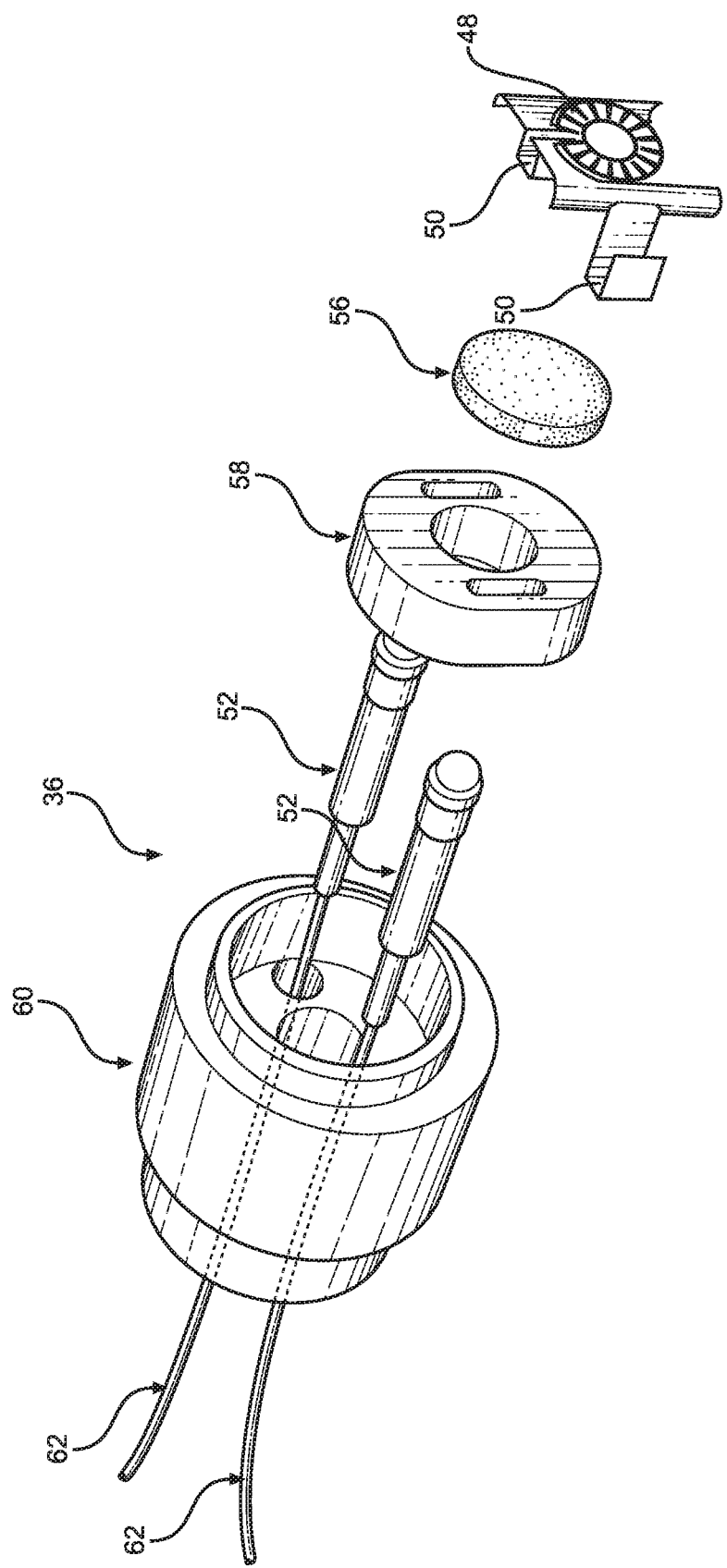

VAPORIZING ASSEMBLY AND VAPOR GENERATING DEVICE

RELATED APPLICATION

This application claims priority to provisional application Ser. No. 62/281,804, filed Jan. 22, 2016.

TECHNICAL FIELD

One of the applications of a microfluidic ejection device is to jet a solution on to another device where a secondary function may be performed. A common secondary function is to vaporize a solution using a heater such that the contents of the solution can be vaporized so as to deliver the solution as a gaseous substance. Applications of such technology include, but are not limited to, metering and vaporizing device for electronic cigarettes, vapor therapy, gaseous pharmaceutical delivery, vapor phase reactions for micro-labs, and the like. This document discloses a method for integrating the fluid delivery and vaporization mechanisms into a single microfluidic device for the purposes of further miniaturization, higher precision vapor delivery and cost reduction, as well as operational efficiency.

BACKGROUND AND SUMMARY

When jetting a fluid onto a heated surface it is highly desirable for 100% of the fluid to vaporize so that liquid is not discharged from the vaporizing device. The problem lies in that the vaporizing heater must be small enough to heat up extremely quickly, but yet have enough surface area to catch all fluid and fluid droplets that is being ejected onto it. In a conventional vaporizing device, a fluid wick would be used that would be disposed in a fluid reservoir on one end thereof while touching a heater on a distal end thereof to vaporize fluid wicked from the fluid reservoir. The wick method has no control of how much fluid is vaporized. Thus the amount of fluid vaporized may vary with the amount of negative pressure applied to the vaporizing device. If a conventional heater configuration for vaporizing fluids is used for providing a jetted fluid, the entire wick is heated to the high temperature. Heating the entire wick requires a large amount of energy and may result in degradation of the wick over time.

Another problem with conventional vaporizing devices is that a standard back pressure range is preferred in vaporizing devices to prevent liquid from drooling from the ejection head. A back pressure of about 7 to about 12 kilonewtons per square meter is desirable. However, if a conventional jetting device for the fluid is exposed to a negative pressure the ejection head will begin to drool and not accurately jet fluid therefrom. Accordingly, what is needed is a fluid vaporizing assembly that provides a sufficient back-pressure for vapor applications yet provides a controlled amount of liquid to be vaporized.

In view of the foregoing, one embodiment of the disclosure provides a heater assembly for a vaporizing device, a vaporizing device containing the heater assembly, and a method for vaporizing fluid ejected by an ejection head. The heater assembly for the vaporizing device includes a vapor inlet end and a vapor outlet end, positive and negative electrodes for contact with positive and negative heater terminals on a vaporizing heater, an insulator for electrical insulation between the positive and negative heater terminals, and a wick disposed between the insulator and the vaporizing heater for dispersion of liquid to be vaporized by the vaporizing heater and for back pressure control of the vaporizing device.

Another embodiment of the disclosure provides a vaporizing device that includes a housing body, a mouthpiece attached to the housing body, a heater assembly disposed in the mouthpiece for vaporizing fluid ejected from an ejection head, and a removable fluid ejection assembly attached to the mouthpiece. The fluid ejection assembly includes a fluid container in flow communication with the ejection head. The heater assembly includes a heater element having a fluid collection side and a second side opposite the fluid collection side, and a porous wick adjacent the second side of the heater element.

A further embodiment of the disclosure provides a method for vaporizing a fluid ejected by an ejection head so that substantially all of the fluid ejected by the ejection head is vaporized. The method includes providing a mouthpiece for sucking in vapors generated by a foraminous vaporizing heater, disposing a porous wick adjacent to the vaporizing heater in the mouthpiece, wherein the wick is disposed on a side of the vaporizing heater opposite a side of the vaporizing heater that faces the ejection head so that the wick is heated by the vaporizing heater and collects and vaporizes any fluid passing through the foraminous vaporizing heater.

In some embodiments, the mouthpiece has a cavity therein for the heater assembly, a vapor outlet port disposed adjacent to the vapor outlet end of the heater assembly and one or more air intake ports disposed adjacent to the vapor inlet end of the heater assembly wherein ambient air is drawn through the vaporizing heater and the wick.

In another embodiment, a support housing is attached to the mouthpiece. The support housing includes a fluid reservoir, an ejection head, and logic control for metering the amount of fluid jetted to the vaporizing heater and for activating the vaporizing heater.

In yet another embodiment, there is a provided a vaporizing device housing for containing the support housing, power circuitry, and a power source for the vaporizing device.

In some embodiments, the wick is a resilient, porous material selected from ceramic, sintered metal, metal/ceramic composite materials, wire mesh, steel wool, fiberglass, and the like. The wick is selected to provide a predetermined negative pressure for the vaporizing device.

In some embodiments, the porous wick is disposed between the heater element and an insulator for heater terminals of the heater element.

In some embodiments, the fluid container is a removable fluid container and ejection head assembly.

In some embodiments, the housing body of the vaporizing device includes a power switch, a vapor activation button, and a USB port.

In some embodiments, an amount of negative pressure adjacent the ejection head is reduced by providing air intake ports in the mouthpiece to provide air flow between the ejection head and the vaporizing heater.

BRIEF DESCRIPTION OF THE DRAWINGS

Other features and advantages of the inventive may be evident by reference to the following detailed description, drawings and claims wherein:

FIG. 4 is an exploded perspective view, not to scale, of interior components of the housing body of FIG. 2;

FIG. 5 is a perspective view, not to scale, of the removable vapor ejection assembly and a removable fluid container for the assembly;

FIG. 9 is an exploded perspective view, not to scale, of a heater assembly component of the vaporizing device disposed in the mouthpiece of FIG. 8 including the vaporizing heater, wick, electrodes and ceramic insulator.

DETAILED DESCRIPTION OF EMBODIMENTS

Figure 1B:
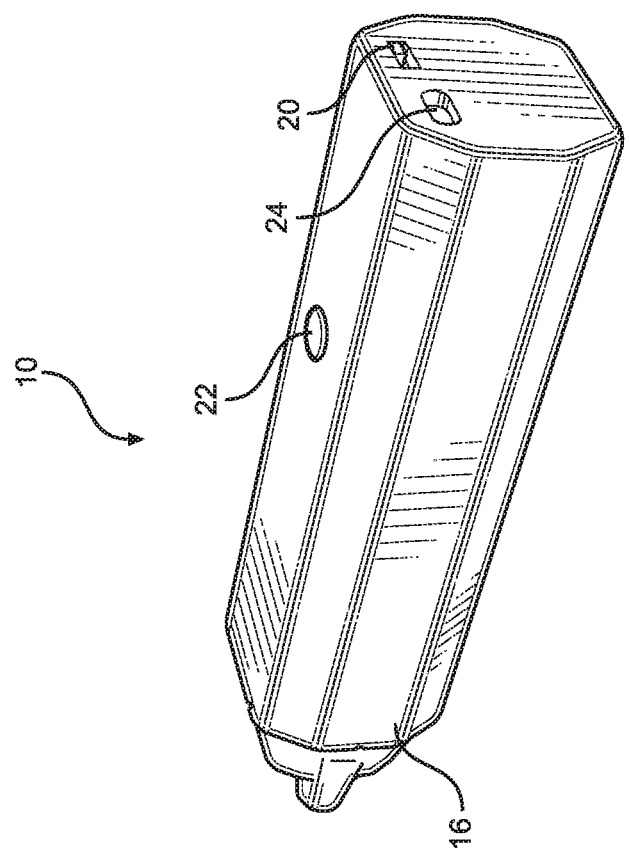
FIGS. 1A-1B are perspective views, not to scale, of a vaporizing device according to the disclosure.
Figure 1A:
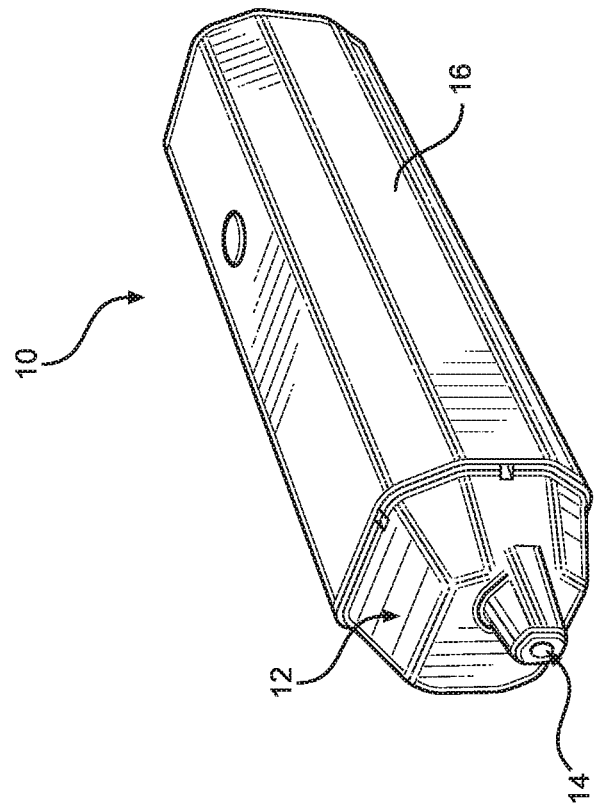
Figure 2:
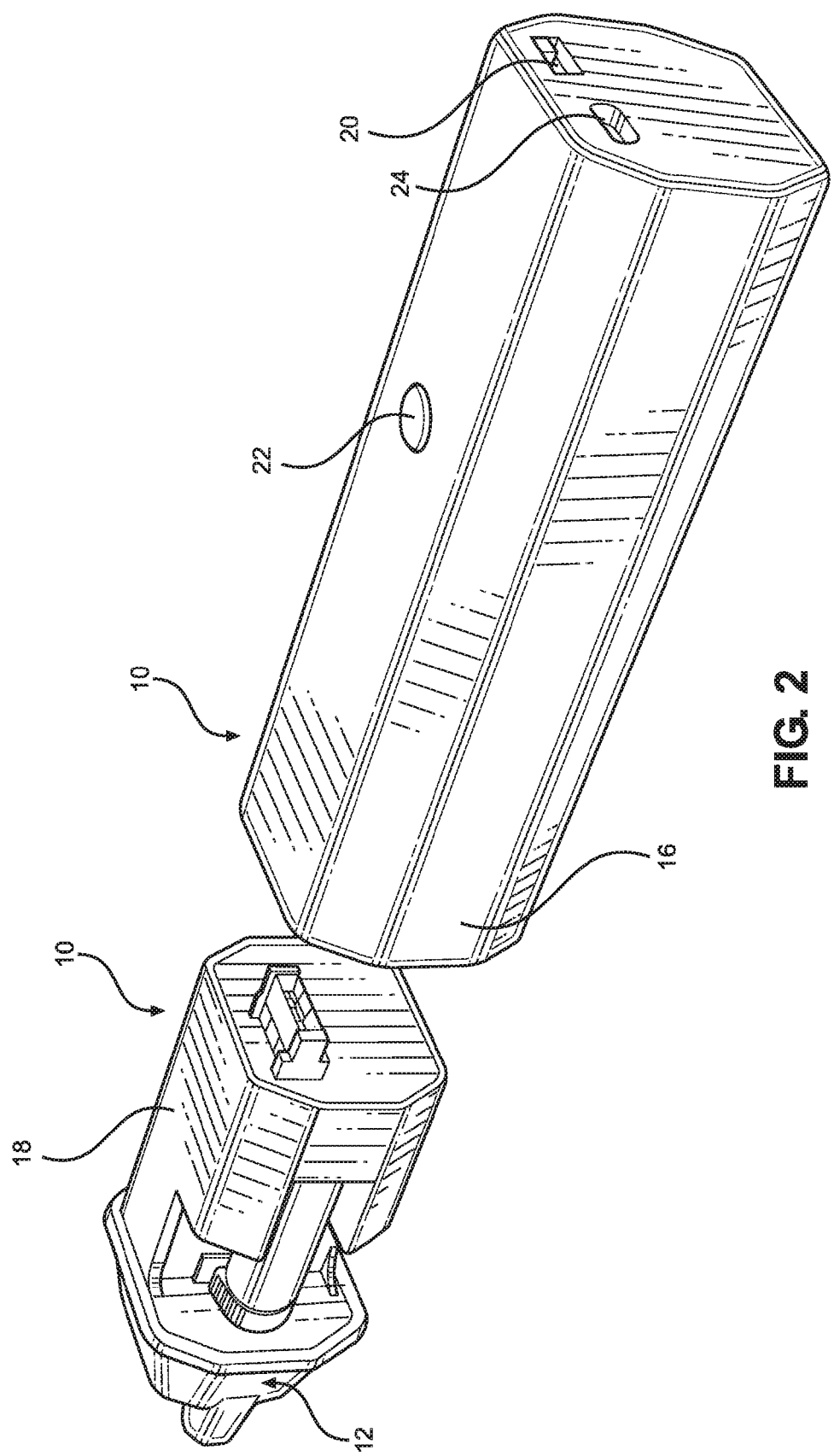
FIG. 2 is an exploded perspective view, not to scale, of the vaporizing device of FIG. 1 showing two main pieces including a housing body, and a removable vapor ejection assembly.

The disclosure is directed to a vaporizing device 10 as shown in FIG. 1 and components therefor as shown in FIG. 2. Such devices 10 may be used for a wide variety of applications wherein a liquid is ejected onto a vaporizing heater to provide a vapor stream as described in more detail below. Such devices 10 are typically hand-held devices such as electronic cigarettes that have a mouthpiece 12 for inhaling vapors generated by the device 10. The mouthpiece 12 may include a vapor exit conduit 14 for flow of vapors out of the device 10. The main components of the device 10 include a housing body 16 and a removable vapor ejection assembly 18 (FIG. 2). The vaporizing device 10 typically includes a power switch, a vapor activation button 22, and an alternative USB connection 24.

The mouthpiece 12, as well as the body 16 of the vaporizing device 10 may be made from a wide variety of materials including plastics, metals, glass, ceramic and the like provided the materials are compatible with the fluids to be ejected and vaporized by the device 10. A particularly suitable material may be selected from polyvinyl chloride, high density polyethylene, polycarbonate, stainless steel, surgical steel, nickel-plated steel, and the like. All parts, including the mouthpiece 12, and body 16 that come in contact with fluids and vapors may be made of plastic. The vapor exit conduit 14 may be made of metal such as stainless steel or other material that is resistant to heat and vapors generated by the device.

Figure 3:
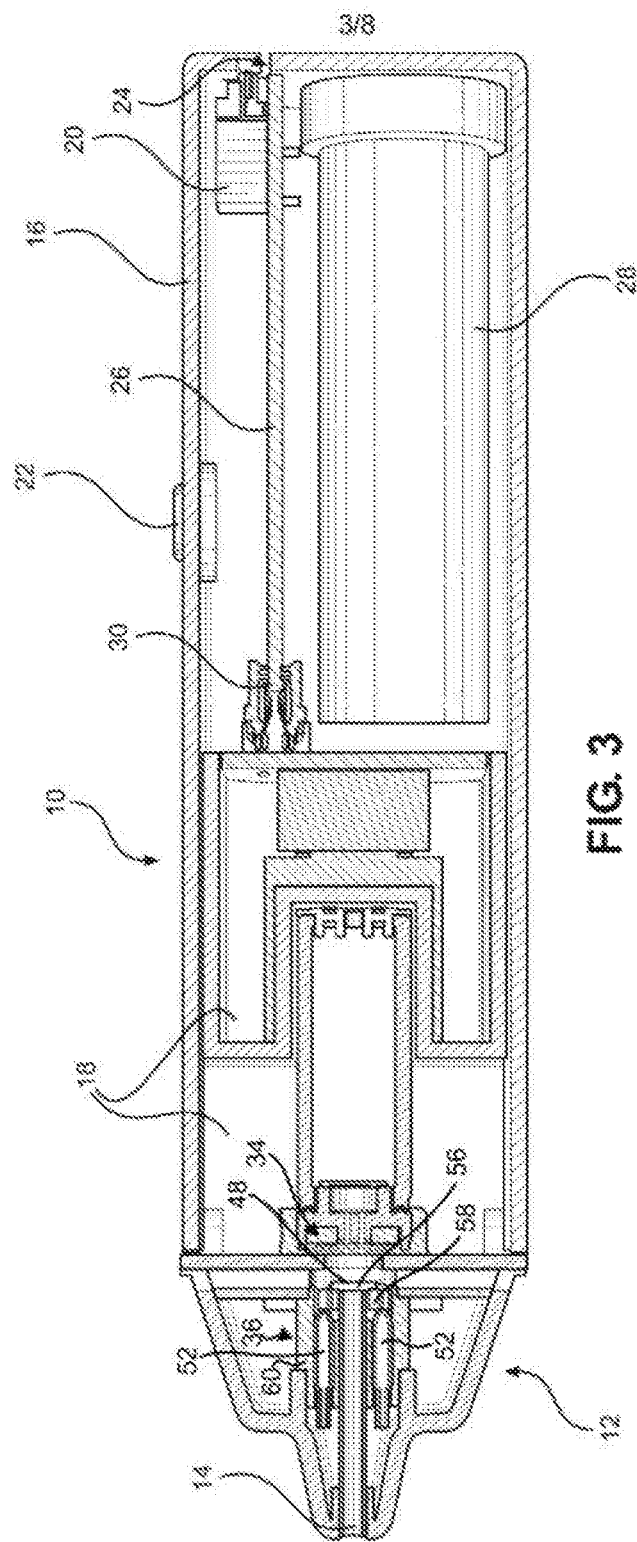
FIG. 3 is a cross-sectional view, not to scale, of the vaporizing device of FIG. 1.

A cross sectional view of the device 10 is shown in FIG. 3 and an exploded view of the housing body 16 is shown in FIG. 4. As shown in FIGS. 3 and 4, the housing body 16 may include a circuit board 26 for providing the logic circuitry for the vaporizing heater and ejection head (described in more detail below). The circuit board 26 is in electrical communication with the vapor ejection assembly 18, the power switch 20 and the USB connection 24. A power source such as a rechargeable battery 28 may also be housed in the housing body 16. Electrical contacts 30 (FIG. 4) may be provided on the circuit board 26 for electrical communication with the removable vapor ejection assembly 18. The USB connection 24 may be used to recharge the battery 28 and to change program setting for the ejection head and vaporizing heater.

Figure 6:
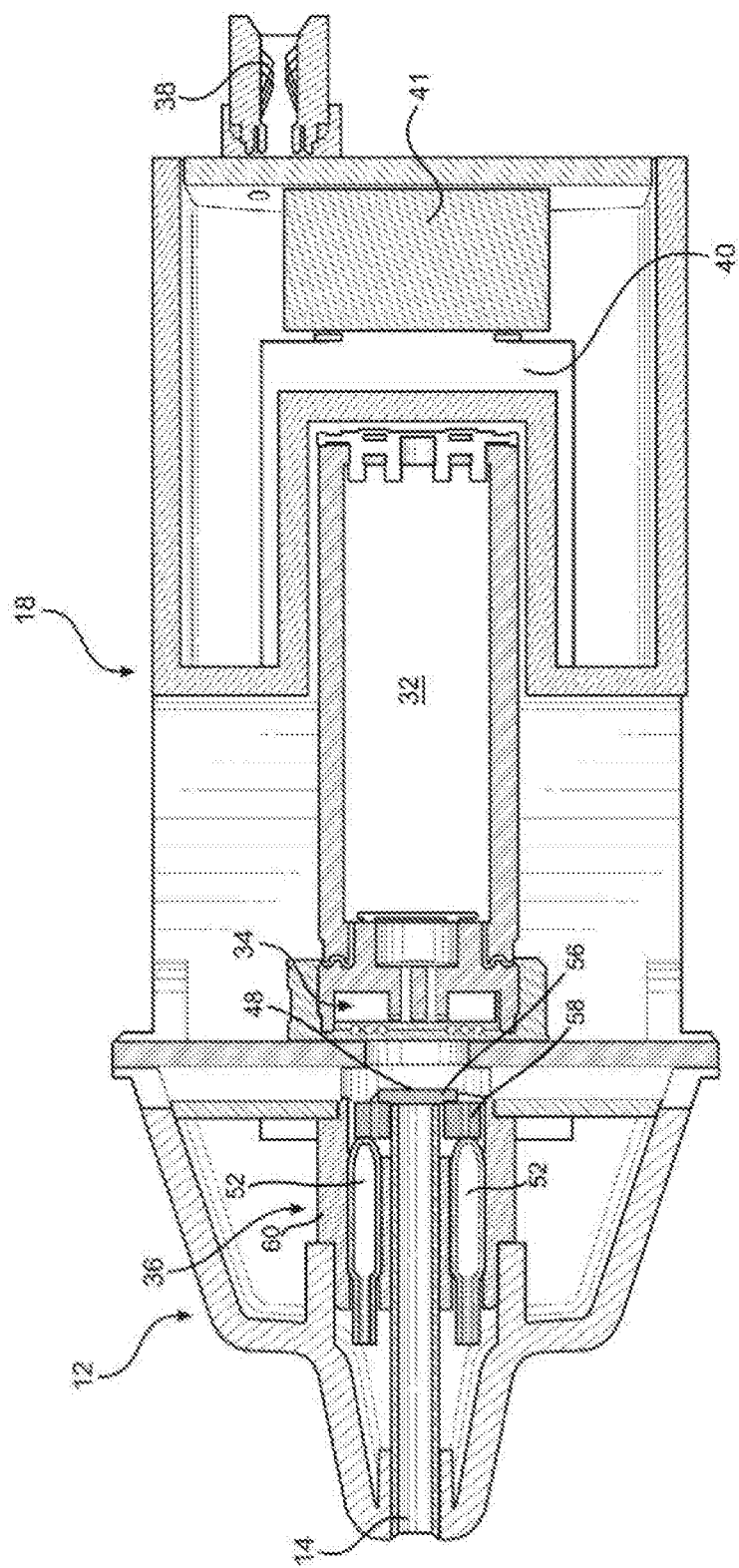
FIG. 6 is a cross-sectional view, not to scale, of the removable vapor ejection assembly of FIG. 5.

An important component of the vaporizing device is the removable vapor ejection assembly 18 shown in more detail in FIGS. 5 and 6. The removable vapor ejection assembly 18 includes a removable fluid container 32 that supplies fluid to be jetted and vaporized by components of the vapor ejection assembly 18. An ejection head 34 is included in the removable ejection assembly 18 and may be disposed on the fluid container 32 or may be disposed adjacent to a heater assembly 36 component of the vapor ejection assembly 18. The ejection head 34 is in fluid flow communication with the fluid container 32 that provides fluid to be ejected by the ejection head 34. An electrical connector 38 is provided on the removable vapor ejection assembly 18 for electrical connection to the circuit board 26 disposed in the housing body 16 for providing power to the ejection head 34.

Figure 7:
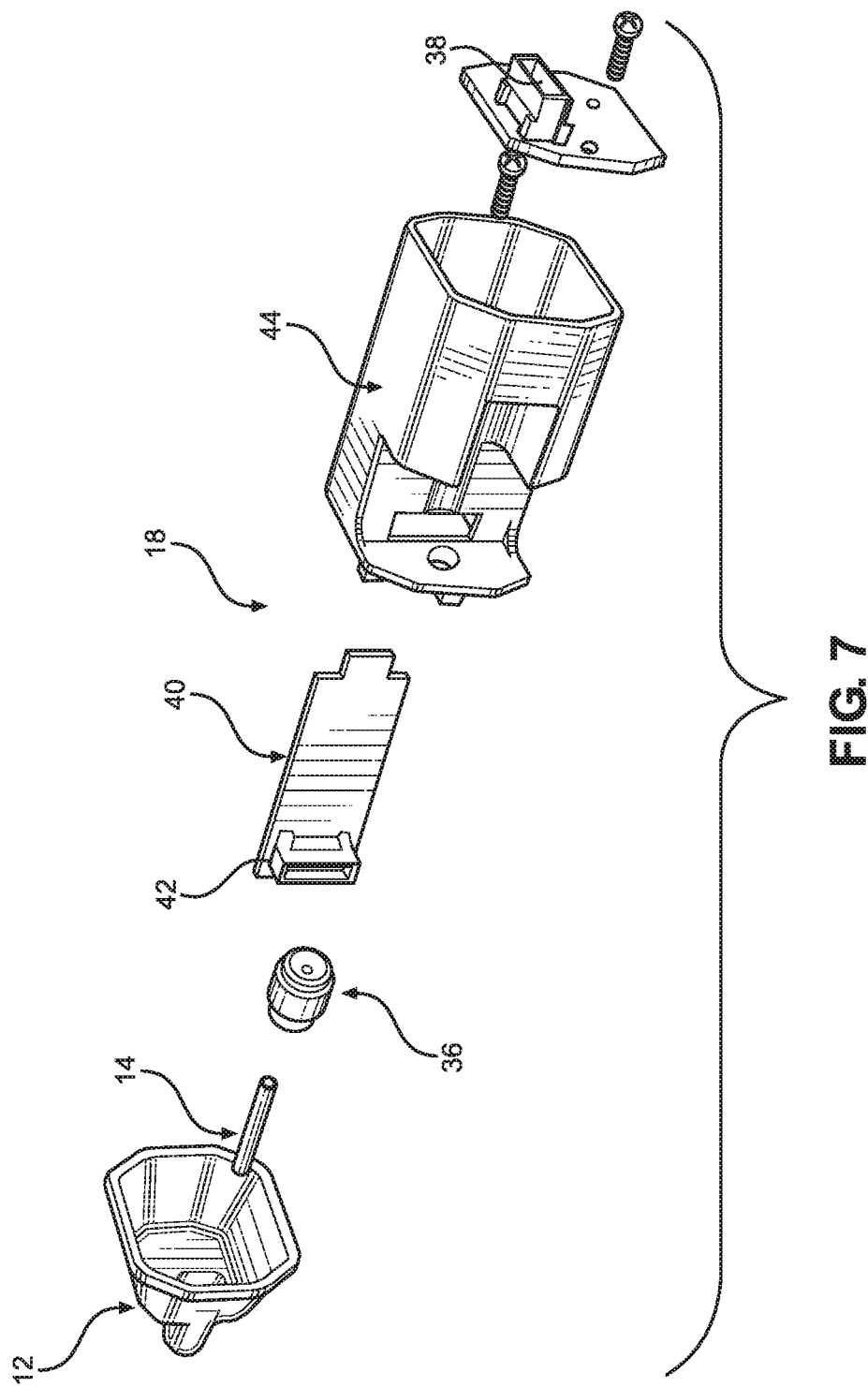
FIG. 7 is an exploded perspective view, not to scale, of the removable vapor ejection assembly of FIG. 5.

An exploded view of portions of the removable vapor ejection assembly 18 is shown in more detail in FIG. 7. Power is provided to the ejection head 34 on the fluid container 32 by a circuit board 40 that is in electrical power communication with a female plug 42 for the fluid container 32. An electrical connector 41 is provided for connecting the circuit board 40 to the power source in the housing body 16. The circuit board 40 may also provide power from the battery 28 to the vaporizing heater in the heater assembly 36. A support housing 44 is provided to hold the components of the vapor ejection assembly 18. The vapor exit conduit 14 may be made of a vapor resistant material such as stainless steel and may have a tubular shape to direct vapor generated by the ejection head through the mouthpiece 12.

Figure 8:
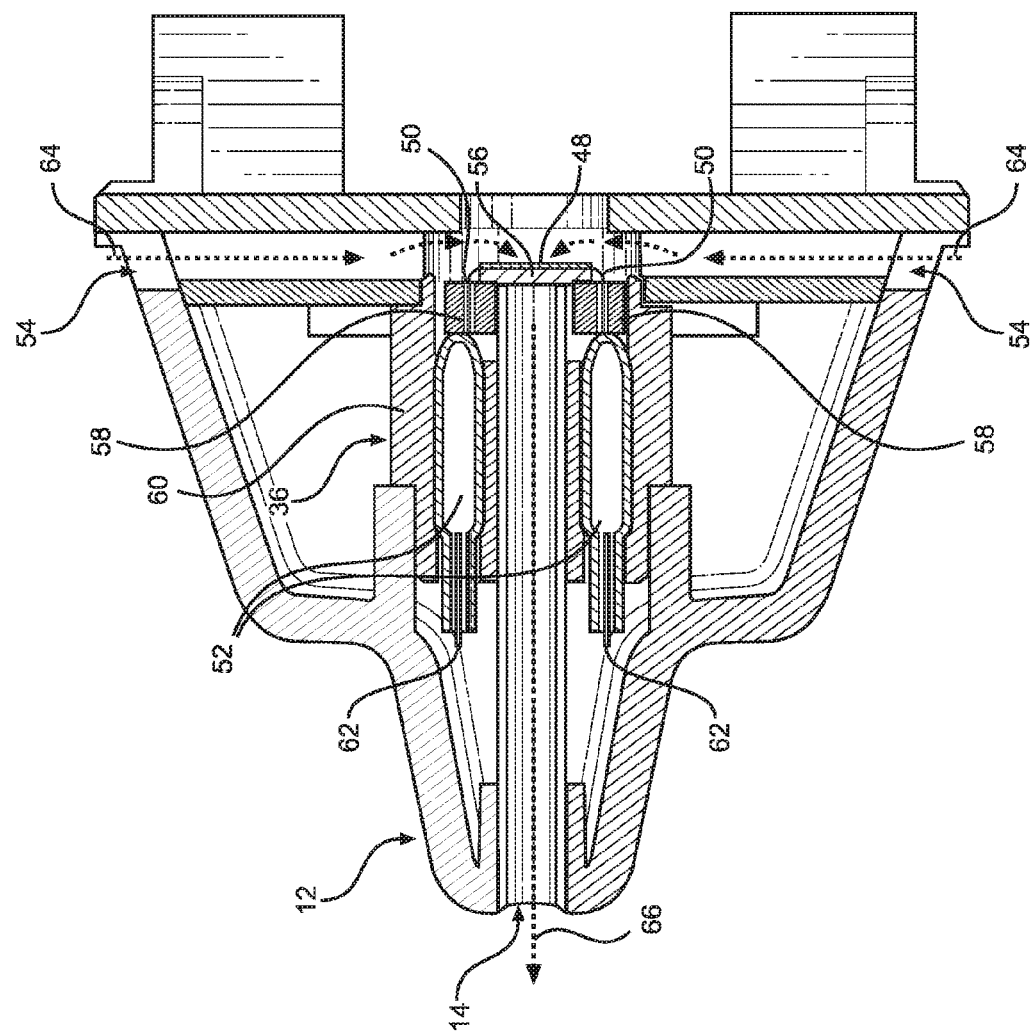
FIG. 8 is a cross-sectional view, not to scale, of a removable mouthpiece for the removable vapor ejection assembly of FIG. 5.

As shown in FIGS. 7 and 8, the vapor ejection assembly 18 may include a mouthpiece 12 that may be removably attached to the support housing 44. The mouthpiece 12 may house the vapor exit conduit 14, the heater assembly 36 that includes a vaporizing heater 48, electrical contact terminals 50 for the heater, electrodes 52, a wick 56, and an insulator 58. The mouthpiece 12 may also include air intake ports 54 therein for maintaining a predetermined backpressure on the ejection head 34. The ejection head 34 ejects fluid from the fluid container 32 onto the vaporizing heater 48 of the heater assembly 36. Logic circuitry within the vaporizing device 10 is configured to jet a predetermined amount of fluid onto the vaporizing heater 48 when the vapor activation button 22 is pushed.

FIG. 9 provides a detail exploded view of the heater assembly 36 which is an important component of the vaporizing device 10. As shown in FIG. 9, the heater assembly is made up of 5 major components namely, the vaporizing heater 48 with positive and negative electrical contact terminals 50, the wick 56, the insulator 58, positive and negative electrodes 52, and a heater housing 60. Positive and negative electrical leads 62 are connected to the electrodes 52 for providing power to the vaporizing heater 48. The vaporizing heater 48 is a foraminous or perforated heating element that enables fluid to be jetted from the ejection head 34 onto the surfaces of the vaporizing heater 48 and through the vaporizing heater 48 onto the surface of the wick 56 that is facing the heater 48. The vaporizing heater 48 is typically a stainless steel heating element having positive and negative electrical contact terminals 50 for electrical connection to a power source in the housing body 16. Fluid from the ejection head 34 is vaporized by the vaporizing heater 48 so that the vapors flow through the heater assembly 36 through an inlet end thereof to an outlet end thereof and out of the vapor exit conduit 14. The heater housing 60 may be made from a wide variety of materials including plastics, ceramics, glass and the like that is resistant to heat and vapors. A suitable material for the heater housing 60 may be a polycarbonate material or a high density polyethylene material.

The wick 56 is a porous material, described in more detail below, that provides an important function in the operation of the vaporizing device 10. The wick 56 in combination with air intake ports 54 in the mouthpiece 12 enable operation of the vaporizing device 10 without imposing a negative pressure adjacent the fluid discharge side of the ejection head 34. Avoiding a negative pressure adjacent the ejection head 34 is important in order to prevent excessive liquid from discharging from the ejection head 34. Thus the correct placement of the porous wick 56 in the heater assembly 36 is important and must be down stream of the air intake ports 54. If the porous wick 56 were positioned in contact with the ejection head 34, liquid would be caused to drool out of the ejection head 34 and the air intake ports 54 would be ineffective for maintaining atmospheric pressure adjacent the discharge side of ejection head 34. Accordingly, the flow of fluid from ejection head 34 is suitably across an air gap between the ejection head 34 and the heater 48 wherein ambient air is introduced to maintain atmospheric pressure adjacent the discharge side of the ejection head 34 regardless of the negative pressure imposed by a user on the vapor exit conduit 14 through the porous wick 56 and vaporizing heater 48.

Also by placing the vaporizing heater 48 between the ejection head 34 and the porous wick 56, fluid ejected from the ejection head 34 that does not impact on the surface of the vaporizing heater 48 will be disposed on the surface of the porous wick 56 adjacent the heater 48. Since the porous wick 56 is in contact with the vaporizing heater 48, the fluid on the surface of the wick 56 will also be vaporized so that no liquid is discharged through the vapor exit conduit 14. All of the pressure drop imposed by the vapor exit conduit 14 is thus taken through the porous wick 56 without imposing a negative pressure adjacent the discharge side of the ejection head 34. In one embodiment, the pressure drop through the wick may range from about 10 to about 100 cm water column.

The wick 56 may be made of a variety of resilient materials including ceramic, sintered metal, composite ceramic and metal materials, wire mesh, steel wool, fiberglass, and the like. As shown in FIG. 9, the wick 56 is disposed between the vaporizing heater 48 and the insulator 58 which may be a ceramic or glass insulator. In order to capture the liquid that may pass through the vaporizing heater 48, the wick 56 is desirably the same size or diameter of the vaporizing heater 48. The thickness of the wick 56 may vary depending on the material selected for the wick 56 so that the desired pressure drop through the wick 56 is obtained. Since the wick 56 acts as a natural insulator as well as a wicking device only the outer surface facing the ejection head 34 gets hot and vapor passes through wick 56 to the ceramic insulator side of the wick 56 before exiting the vaporizing device 10. The insulator 58 on the vapor exit side of the wick 56 initiates a cooling cycle for the vapor that passes through the wick 56. The wick material and configuration may be selected so that the wick density can be used to establish a negative pressure in the vaporizing device without effecting the pressure adjacent the ejection head 34 that delivers fluid to the vaporizing heater 48.

As air is drawn through the vapor exit conduit 14, air is also drawn in through air intake ports 54 that are upstream of the vaporizing heater 48 so that the jetted fluid is focused onto the vaporizing heater 48 without disrupting the jetted fluid flow. All fluid from the ejection head 34 is jetted onto vaporizing heater 48 and/or wick 56 due to the direction of air flow through the vaporizing heater 48 and wick 56 indicated by arrows 64 and 66 (FIG. 8).

Accordingly, the foregoing configuration of vaporizing heater 48, wick 56 and air intake ports 54 work in conjunction with one another to improve the efficiency of vaporization of fluid from the ejection head 34 and reduce or eliminate any drooling of liquid from the ejection head 34.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A heater assembly for a vaporizing device comprising a vapor exit conduit, positive and negative electrodes for contact with positive and negative heater terminals on a vaporizing heater and for electrical connection to logic circuitry for activating the vaporizing heater, an insulator for electrical insulation between the positive and negative heater terminals, and a wick disposed between the insulator and the vaporizing heater for dispersion of liquid jetted to the vaporizing heater and wick from an ejection head that is activated by the logic circuitry, wherein the wick provides pressure control of the vaporizing device and the vaporizing heater is between the wick and the ejection head.

2. The heater assembly of claim 1, further comprising a mouthpiece for the vaporizing device, the mouthpiece having a cavity therein for the heater assembly, wherein the mouthpiece is disposed adjacent to the vapor exit conduit of the heater assembly, and one or more air intake ports disposed adjacent to the heater assembly wherein ambient air is drawn through the vaporizing heater and the wick.

3. The heater assembly of claim 1, further comprising a support housing attached to the mouthpiece, the support housing comprising a fluid reservoir, the ejection head, and the logic circuitry for metering the amount of fluid jetted to the vaporizing heater and for activating the vaporizing heater.

4. The heater assembly of claim 3, further comprising a vaporizing device housing for containing the support housing, power circuitry, and a power source.

5. The heater assembly of claim 1, wherein the wick is selected to provide a predetermined negative pressure for the vaporizing device.

6. The heater assembly of claim 5, wherein the wick comprises a resilient, porous material selected from the group consisting of ceramic, sintered metal, metal/ceramic composite materials, wire mesh, steel wool, and fiberglass.

7. A vaporizing device comprising the heater assembly of claim 1.

8. A vaporizing device comprising a housing body, a mouthpiece attached to the housing body, a heater assembly disposed in the mouthpiece for vaporizing fluid jetted from an ejection head, and a removable fluid ejection assembly attached to the mouthpiece, wherein fluid ejection assembly comprises a fluid container in flow communication with the ejection head, and wherein the heater assembly comprises a heater element having a fluid collection side and a second side opposite the fluid collection side, and a porous wick adjacent the second side of the heater element, wherein the ejection head is disposed toward the fluid collection side of the heater element.

9. The vaporizing device of claim 8, wherein the porous wick is disposed between the heater element and an insulator for electrical leads to the heater element.

10. The vaporizing device of claim 8, wherein the mouthpiece further comprises air intake ports for providing air adjacent the ejection head and between the ejection head and the heater element.

11. The vaporizing device of claim 8, wherein the fluid container comprises a removable fluid container and ejection head assembly attached to the removable fluid container.

12. The vaporizing device of claim 8, wherein the housing body further comprises a circuit board disposed within the housing body, wherein the circuit board is in electrical communication with a power switch, a vapor activation button, and a USB port disposed on the circuit board.

13. A method for vaporizing a fluid jetted by an ejection head so that substantially all of the fluid jetted by the ejection head is vaporized, comprising providing a mouthpiece for sucking in vapors generated by a foraminous vaporizing heater, disposing a porous wick adjacent to the vaporizing heater in the mouthpiece, wherein the wick is disposed on a side of the vaporizing heater opposite a side of the vaporizing heater that faces the ejection head so that the wick is heated by the vaporizing heater and collects and vaporizes any fluid passing through the foraminous vaporizing heater.

14. The method of claim 13, further comprising reducing an amount of negative pressure adjacent the ejection head by providing air intake ports in the mouthpiece to provide air flow between the ejection head and the vaporizing heater.

15. The method of claim 13, wherein the wick comprises a resilient, porous material selected from the group consisting of ceramic, sintered metal, metal/ceramic composite materials, wire mesh, steel wool, and fiberglass.

* * * * *